US 9,164,027 B2

(12) United States Patent
Nieuwland et al.

(10) Patent No.: US 9,164,027 B2
(45) Date of Patent: Oct. 20, 2015

(54) FREQUENCY TUNABLE LASER SYSTEM

(71) Applicant: Nederlandse Organisatie voor toegepast-natuurwetenschappelijk onderzoek TNO, Delft (NL)

(72) Inventors: Remco Alexander Nieuwland, Delft (NL); Bart Michiel De Boer, Delft (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 0 days.

(21) Appl. No.: 14/395,291

(22) PCT Filed: Apr. 17, 2013

(86) PCT No.: PCT/NL2013/050276
§ 371 (c)(1),
(2) Date: Oct. 17, 2014

(87) PCT Pub. No.: WO2013/157942
PCT Pub. Date: Oct. 24, 2013

(65) Prior Publication Data
US 2015/0116724 A1    Apr. 30, 2015

(30) Foreign Application Priority Data

Apr. 18, 2012  (EP) .................................. 12164645

(51) Int. Cl.
*H01S 3/10* (2006.01)
*G01N 21/25* (2006.01)
(Continued)

(52) U.S. Cl.
CPC ............. *G01N 21/255* (2013.01); *G01J 9/0246* (2013.01); *H01S 3/13* (2013.01);
(Continued)

(58) Field of Classification Search
USPC ...................... 372/20, 22, 25, 28, 29.014, 30
See application file for complete search history.

(56) References Cited

U.S. PATENT DOCUMENTS 4,592,058 A  *  5/1986  Mongeon et al. ................ 372/32
2004/0245441 A1*  12/2004  Pieterse et al. ........... 250/227.14
(Continued)

OTHER PUBLICATIONS

International Search Report—PCT/NL2013/050276—Mailing Date Jan. 7, 2013.
(Continued)

*Primary Examiner* — Dung Nguyen
(74) *Attorney, Agent, or Firm* — Banner & Witcoff, Ltd.

(57) ABSTRACT

There is provided a frequency tunable laser system comprising a laser, frequency varying means arranged for varying an optical frequency output of the laser, an intensity sensor arranged for receiving light from the laser, and a processor arranged for controlling the frequency varying means for varying the optical frequency output of the laser and receiving an intensity signal from the intensity sensor for monitoring the intensity output of the laser. The frequency tunable laser system further comprises an external reflective surface, in use, fixedly arranged in a light path of the laser beam outside the laser cavity at a predefined distance from the second reflective surface along the light path of the laser beam to reflect part of the emitted laser beam back into the laser cavity. The processor is further arranged for processing the intensity signal and registering oscillations of the intensity output caused by interference of the reflected part of the laser beam in the cavity and responsive to a change in optical frequency and calculating the change in optical frequency output from the registered oscillations of the intensity output and predefined distance.

15 Claims, 12 Drawing Sheets

(51) Int. Cl.
*H01S 5/062* (2006.01)
*H01S 5/14* (2006.01)
*G01J 9/02* (2006.01)
*H01S 3/13* (2006.01)
*H01S 5/00* (2006.01)
*H01S 5/0687* (2006.01)

(52) U.S. Cl.
CPC ............... *H01S 5/0622* (2013.01); *H01S 5/14* (2013.01); *G01N 2201/06113* (2013.01); *G01N 2201/08* (2013.01); *G01N 2201/12* (2013.01); *H01S 5/0014* (2013.01); *H01S 5/0687* (2013.01)

(56) References Cited

U.S. PATENT DOCUMENTS

2005/0134861 A1 6/2005 Kringlebotn et al.
2006/0131488 A1 6/2006 Thingbo et al.
2010/0296089 A1 11/2010 Webb et al.
2011/0058183 A1* 3/2011 Nakajima .................... 356/625

OTHER PUBLICATIONS

Tucker Jr et al: "Effect of Multiple Transverse Modes in Self-Mixing Sensors Based on Vertical-Cavity Surface-Emitting Lasers"1 Applied Optics. Optical Society of America. Washington. DC; US. vo 1 • 46. No. 4. Feb. 1, 2007. pp. 611-619. XP001504413. ISSN: 0003-6935. DOI: 10.1364/A0.46.000611 pp. 612. 617.

Giuliani: "Laser Diode Self-Mixing Technique for Sensing Applications", j. Opt. A: Pure Appl. Opt., vol. 4, 2002, pp. S283-S294, XP002510274, Cited in the Application pp. S28-S285; Figure 1.

Suleiman et al.: "FBG-Based Dynamic Strain Sensors Demodulated by Self-Mixing Interferometry: Improving Strain Measurement Resolution", International Instrumentation and Measurement Technology Conference I2MTC 2009, Singapore May 5-7, 2009.

* cited by examiner

FREQUENCY TUNABLE LASER SYSTEM

CROSS-REFERENCE TO RELATED APPLICATIONS

This application is a U.S. National Stage application under 35 U.S.C. §371 of International Application PCT/NL2013/050276 (published as WO 2013/157942 A1), filed Apr. 17, 2013, which claims priority to Application EP 12164645.9, filed Apr. 18, 2012. Benefit of the filing date of each of these prior applications is hereby claimed. Each of these prior applications is hereby incorporated by reference in its entirety.

FIELD AND BACKGROUND OF THE INVENTION

The present invention relates to the field of laser systems, in particular to a frequency tunable laser system for use in an optical measuring system. The present invention further relates to a method for tuning a frequency tunable laser system.

Optical measuring systems may be used to perform measurements of optical properties as a function of optical frequency. One example of an optical measuring system may employ an optical sensing element e.g. comprising a Fiber Bragg Grating (FBG) or ring resonator or Fabry-Perot sensor. Such an optical sensing element may exhibit a spectral signature that varies as a function of a physical parameter influencing the sensing element. In order to use the optical sensing element to quantify the physical parameter, a measurement of the spectral signature of the optical sensing element is desired.

Measuring the spectral signature of an optical sensing element may comprise probing the optical sensing element with a varying narrowband optical signal and recording the spectral response of the sensing element. The varying narrowband optical signal may be generated by passing a broadband optical signal through a narrowband scanning filter. Alternatively, the narrowband optical signal may be directly generated, e.g. by a tunable narrowband laser diode. In a scan, the optical frequency of the narrowband optical signal may be varied through a range of probing frequencies and a resulting response of the optical sensing element may be recorded. In order to accurately reconstruct the spectral signature of the sensing element, it is desired to measure and/or calculate the optical frequency of the narrowband optical signal, e.g. during the scan or afterwards.

US2005/0134861 discloses a method for determining optical wavelengths, such as the Bragg wavelengths of an FBG sensor array. Wavelength-swept light having a characteristic spectrum is swept over a bandwidth and is applied to an interference filter. The interference filter produces an optical spectrum having one or more reference peaks that are identifiable because of the characteristic spectrum. The optical spectrum is converted into electrical signals having at least one electrical signal that is identifiable because of the characteristic spectrum. The identifiable electrical signal is used by a signal processor as an absolute wavelength reference.

There is a desire for a frequency tunable laser system of simpler design.

SUMMARY OF THE INVENTION

In a first aspect there is provided a frequency tunable laser system comprising a laser with first and second reflective surfaces defining a laser cavity with a laser gain medium between the first and second reflective surfaces, wherein the second reflective surface is semi-transparent for emitting, in use, a laser beam from the second surface; frequency varying means arranged for varying an optical frequency output of the laser; an intensity sensor arranged for receiving light from the laser and providing an intensity signal that is indicative of an intensity output of the light from the laser; a processor arranged for controlling the frequency varying means for varying the optical frequency output of the laser; and receiving the intensity signal from the intensity sensor for monitoring the intensity output of the laser; wherein the frequency tunable laser system further comprises an external reflective surface, in use, fixedly arranged in a light path of the laser beam outside the laser cavity at a predefined distance from the second reflective surface along the light path of the laser beam to reflect part of the emitted laser beam back into the laser cavity; and wherein the processor is further arranged for processing the intensity signal and registering oscillations of the intensity output caused by interference of the reflected part of the laser beam in the cavity and responsive to a change in optical frequency; and calculating the change in optical frequency output from the registered oscillations of the intensity output and predefined distance.

While known frequency tunable laser systems may employ a separate interference filter to produce frequency spaced reference peaks, the currently disclosed system uses self-mixing interference to provide a periodic frequency reference signal. In this way the separate interference filter of known frequency tunable laser systems may be dispensed with and a frequency tunable laser system of simpler design may be provided. The presently disclosed frequency tunable laser system may comprise less optical components which may lead to savings in parts and/or a more compact setup. This in turn allows for further miniaturization of the frequency tunable laser system Self-mixing interferometry in laser systems may be known as such e.g. from J. Opt. A: Pure Appl. Opt. 4 (2002) S283-S294, "Laser diode self-mixing technique for sensing applications" by Giuliani et al. However, this article discloses using self-mixing in a fixed frequency laser for detecting a varying path length between the laser and a moving reflective surface. This is notably different in purpose and implementation from the presently disclosed frequency tunable laser system wherein the path length of the reflective surface is fixed.

In an embodiment, there is provided an optical measuring system comprising a frequency tunable laser system according to the first aspect; and further comprising a sensor comprising an optical sensing element arranged for receiving output from the laser system and transmitting and/or reflecting a sensing output comprising a frequency spectrum signature; a sensing detector arranged for receiving the transmitted and/or reflected sensing output; wherein the processor is further arranged for reading out the sensing detector as a function of the varying optical frequency output of the laser; and recording the optical sensing element frequency spectrum. By using the frequency tunable laser system according to the first aspect, an optical measuring system of simpler design may be provided. The presently disclosed optical measuring system may comprise less optical components which may lead to savings in parts and/or a more compact setup. This in turn allows for further miniaturization of optical measuring system.

In a further embodiment there is provided an optical measuring system, wherein the sensing element spectral signature is dependent on a physical parameter of the optical sensing element, the optical measuring system further comprising a lookup table comprising correlations between the sensing element spectral signature and the physical parameter; wherein the processor is further arranged for using the lookup table to calculate the physical parameter. The optical measuring system according to this embodiment may be used to monitor a physical parameter.

In a second aspect there is provided a method for tuning a frequency tunable laser system comprising a laser with first and second reflective surfaces defining a laser cavity with a laser gain medium between the first and second reflective surfaces, wherein the second reflective surface is semi-transparent for emitting, in use, a laser beam from the second surface; frequency varying means arranged for varying an optical frequency output of the laser; an intensity sensor arranged for receiving light from the laser and providing an intensity signal that is indicative of an intensity output of the light from the laser; the method comprising controlling the frequency varying means for varying the optical frequency output of the laser; and receiving the intensity signal from the intensity sensor for monitoring the intensity output of the laser; wherein the frequency tunable laser system further comprises an external reflective surface, in use, fixedly arranged in a light path of the laser beam outside the laser cavity at a predefined distance from the second reflective surface along the light path of the laser beam to reflect part of the emitted laser beam back into the laser cavity; and wherein the method further comprises processing the intensity signal and registering the oscillations of the intensity output caused by interference of the reflected part of the laser beam in the cavity and responsive to the change in optical frequency; and calculating the change in optical frequency output from the registered oscillations of the intensity output and predefined distance.

BRIEF DESCRIPTION OF THE DRAWINGS

These and other features, aspects, and advantages of the apparatus, systems and methods of the present invention will become better understood from the following description, appended claims, and accompanying drawing wherein:

DETAILED DESCRIPTION

Figure 1:
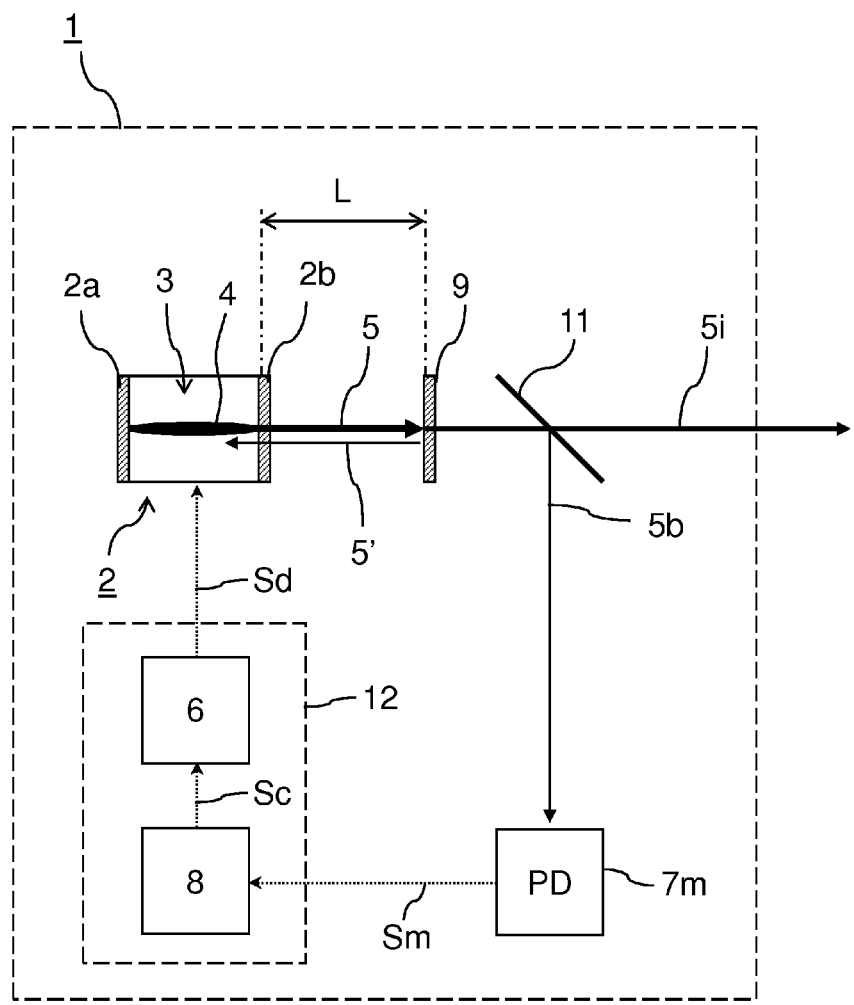
FIG. 1 shows a first embodiment of a frequency tunable laser system.

The following detailed description is merely exemplary in nature and is in no way intended to limit the invention, its application, or uses. The description is therefore not to be taken in a limiting sense, and the scope of the present system is defined only by the appended claims. In some instances, detailed descriptions of well-known devices and methods may be omitted so as not to obscure the description of the present system. Terminology familiar to those skilled in the art of the current subject matter may not be explicitly defined and instead be apparent in light of the teaching, context, and examples of the description and drawings.

To characterize the wavelength response of an optical system (as is for instance done when interrogating a network of optical sensors), a narrow-band scanning source, i.e. a light source of which the wavelength is varied during scanning, may be used. For accurate results, the wavelength of the source during the scan can be determined. An interferometer, used to track the change in wavelength, combined with an absolute reference, e.g. obtained using a reference Fiber Bragg Grating (FBG) with known wavelength, can be employed to track absolute wavelength of the source during a scan.

A conventional system, and the employed interferometer may comprise many interconnected optical elements and may therefore be, large, costly in terms of optical components and requiring electronic sub-systems. Moreover, the complexity may render such a system prone to errors as result of e.g. non-ideal coupling.

The present disclosure relates to a system comprising a self-mixing interferometer rather than a separate interferometer. Self-mixing interferometry may be caused by optical feedback into the laser, obtained by deliberately reflecting a substantial part of the emitted laser light back into the cavity. The optical power fed back may interfere with the light in the (internal) laser cavity and thereby modulate the optical power emitted by the laser. By varying the emitted wavelength or frequency (e.g. by means of laser current modulation) and analyzing the change in emitted optical power, a change in optical frequency may be determined.

By reconfiguration of optical components and/or programming, an interrogator based on self mixing interferometry is disclosed that may reduce the complexity of the total system. E.g. FIG. 8 depicts an embodiment with similar functionality as the system of FIG. 7, at reduced optical component count.

E.g. as a result of the reduced number of photodiodes used, the required electronic system may also be smaller. A detailed description of these figures is provided further below.

It is to be appreciated that teachings of the present disclosure may result in a reduced complexity, cost and/or size of interrogators for optical measuring systems e.g. comprising FBG, Fabry-Perot cavity and/or ring resonator sensors. The current teaching may thus advantageously be applied to miniature laser based sensors systems, e.g. a frequency tunable laser on a chip.

Further advantages and applications of the present disclosure may become more apparent from the following detailed description of the drawings and/or the exemplary embodiments explained with reference thereto. In the description, reference is made to the accompanying drawings which form a part hereof, and in which are shown, by way of illustration, specific embodiments in which the described devices and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present disclosure. In particular, steps and/or parts of the shown embodiments may be omitted and/or added without departing from the scope of the current methods and systems, which scope is defined by the appended claims. This description is therefore to be regarded in an illustrative and non-limiting manner.

In the figures, like reference numerals and symbols may refer to like or similar components, systems, measures and/or steps unless otherwise indicated.

FIG. 1 shows a first embodiment of a frequency tunable laser system 1 comprising a laser 2, a frequency varying means 6, an intensity sensor 7m, and a processor 8.

The laser comprises first 2a and second 2b reflective surfaces defining a laser cavity 3 with a laser gain medium 4 between the first 2a and second 2b reflective surfaces. The second reflective surface 2b is semi-transparent for emitting, in use, a laser beam 5 from the second surface 2b. The frequency varying means 6 is arranged for varying an optical frequency output of the laser 2. The intensity sensor 7m is arranged for receiving light from the laser 2 and providing an intensity signal Sm that is indicative of an intensity output of the light from the laser 2. The processor 8 is arranged for controlling the frequency varying means 6 for varying the optical frequency output of the laser 2 and receiving the intensity signal Sm from the intensity sensor 7m for monitoring the intensity output I of the laser 2. The light may comprise electromagnetic radiation of any frequency, and includes e.g. visible, infrared, and ultraviolet light.

The frequency tunable laser system 1 further comprises an external reflective surface 9, in use, fixedly arranged in a light path of the laser beam 5. The external reflective surface 9 is arrange outside the laser cavity 3 at a predefined distance L from the second reflective surface 2b along the light path of the laser beam. The reflective surface 9 is arranged to reflect part 5' of the emitted laser beam 5 back into the laser cavity 3. The processor 8 is further arranged for processing the intensity signal Sm and registering oscillations of the intensity output I caused by interference of the reflected part 5' of the laser beam 5 in the cavity and responsive to the change in optical frequency; and calculating the change in optical frequency output from the registered oscillations of the intensity output and predefined distance L.

The oscillations of the intensity output of the laser may result from self-mixing in the laser. Self-mixing may refer to the splitting off and recombining of light. Self-mixing in a laser may occur when at least part of the emitted laser light is reflected back into the laser cavity, e.g. by an external reflective surface. The back-reflected light may mix with one or more cavity modes of the laser. The laser power may fluctuate as a result of e.g. constructive or destructive interference between the cavity modes and the back-reflected light. These fluctuations may depend on a phase of the light that re-enters the cavity, e.g. relative to a phase of the cavity modes. The phase of the back-reflected light may depend on the frequency/wavelength of the light and the distance it has traveled outside the cavity, e.g. the round-trip distance. The phase may also depend on a phase velocity of the light as it travels outside the laser cavity.

Light of the laser 2 may be split into two beams 5i and 5b by beam splitter 11. Beam 5i may be used e.g. for interrogating an optical sensor. Beam 5b is used for measuring the oscillations in the laser intensity output for determining a change in optical frequency of the laser. The beam splitter may comprise e.g. a semi-transparent mirror. The light beams may be directed through one or more media such as optical fibers for controlling an optical path of the light beams. In an embodiment, fiber optic couplers may be used for splitting or combining light beams. The optical fibers may comprise optically active elements or structures having a frequency dependent response, e.g. FBGs may be comprised in a fiber.

The laser 2 preferably comprises a diode laser. An advantage of a diode laser may lie in its compactness and robustness. However also other types of lasers, influenced by self-mixing interference, may be used in the presently disclosed systems and methods. E.g. a gas laser, or flash-light/diode pumped laser may be used.

The processor 8 may include micro-processors, central processing units (CPUs), digital signal processors (DSPs), ASICs, or any other processor(s) or controller(s) such as digital optical devices, or analog electrical circuits that perform the same functions, and employ electronic techniques and architecture. The processor is typically under software control for example, and has or communicates with a memory that stores software and other data such as preferences, parameters, et cetera. The processor 8 and frequency varying means 6 may be comprised in integrated electronics 12 or may comprise dedicated components that may themselves be split into further components.

Figure 2:
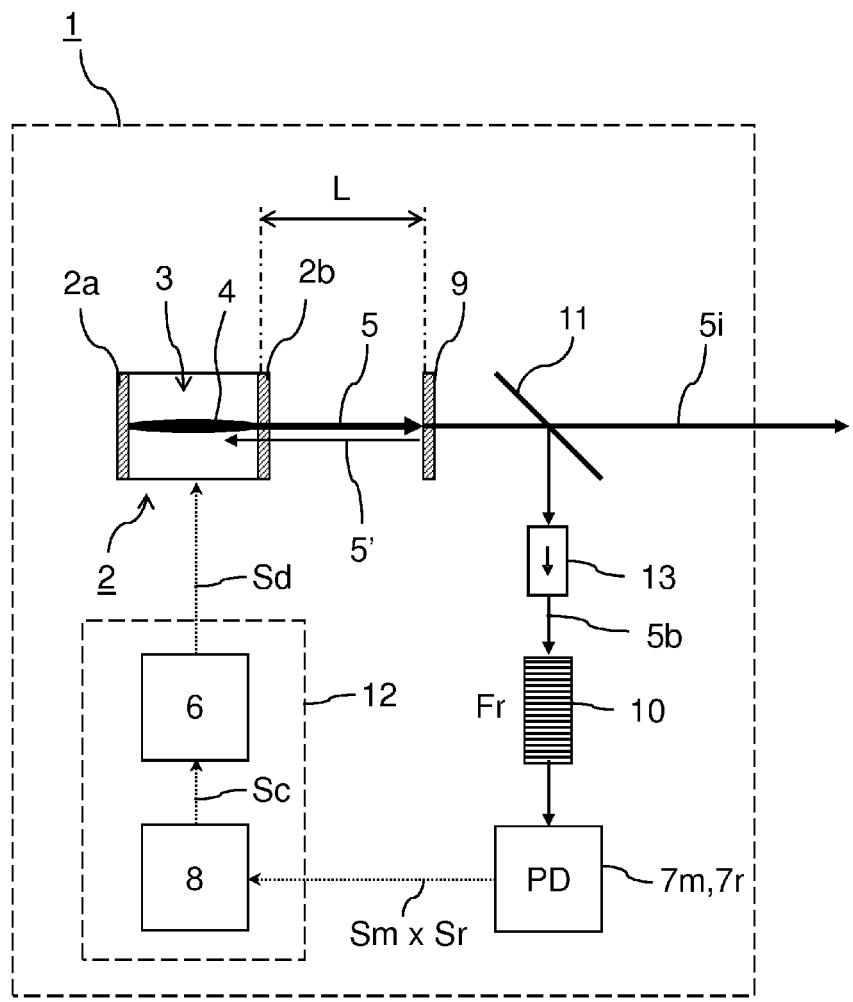
FIG. 2 shows a second embodiment of a frequency tunable laser system.

FIG. 2 shows a second embodiment of a frequency tunable laser system 1 similar to FIG. 1 and further comprising a referencing means. The referencing means is arranged for providing the processor 8 with a reference frequency Fr during the varying of the optical frequency output of the laser 2. The processor is further arranged for calculating the optical frequency output of the laser by tracking the change in optical frequency output relative to the reference frequency Fr.

In the present embodiment, the referencing means comprises a reference filter 10 and a reference sensor 7r. The reference filter 10 is arranged in a light path 5b of the laser 2. The reference filter 10 has a reference filter frequency spectrum comprising a reference spectral signature at the reference frequency Fr. The reference sensor 7r is arranged for registering the reference filter frequency spectrum during the varying of the optical frequency output F of the laser 2, and providing the processor 8 with the reference frequency Fr when the reference spectral signature Pr is detected.

Preferably, the frequency tunable laser system 1, further comprises an optical isolator 13 arranged in a light path of the laser beam for preventing back-reflections from components, other than the external reflective surface 9, such as the referencing filter 10, into the cavity 3. The optical isolator 13 may e.g. prevent a reflection off the referencing filter 10 which may occur at frequency Fr from reentering the laser cavity. Alternatively or in addition any other means such as a circulator may be provided for preventing unwanted reflections and other light signals of components other than the external reflective surface 9 to reenter the laser cavity 3. While in the presently shown embodiment, the optical isolator 13 is arranged in a side path 5b of the laser just before the referencing filter 10, the optical isolator 13 or other means for preventing unwanted reflections may also be arranged elsewhere, e.g. in the main path of the laser between the external reflective surface 9 and the beam splitter 11.

Figure 6A:
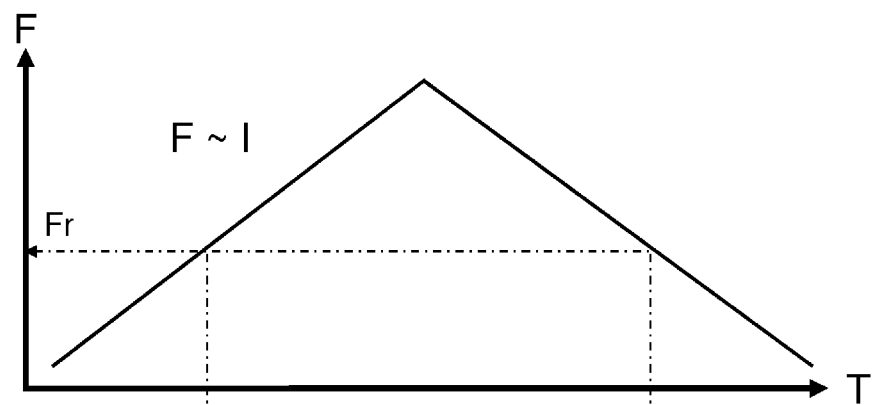
FIG. 6A shows a graph of an optical output frequency and intensity of a frequency tunable laser system varying as a function of time without self-mixing.

Throughout the figures, reference 7m is used to indicate a sensor used for measuring oscillations in the laser intensity output resulting from self-mixing interference. Reference 7r is used to indicate a sensor used for measuring a reference frequency from a referencing filter. Reference 7s (shown in FIG. 7 and further) is used to indicate a sensor used for measuring a spectral signature of a sensing element (see FIG. 7 and further). Throughout the figures, multiple references 7m, 7r, and/or 7s may point to a single sensor that is used for multiple purposes. The signals coming from a combined sensor may comprise a combined signal of the measured responses. For example in the present embodiment of FIG. 2, the sensor 7m, 7r is used for measuring both the oscillations and the reference frequency. The signal Sm×Sr, sent to processor 8 comprises oscillations caused by self-mixing interference and an indication of a reference frequency Fr caused by the referencing means 10, e.g. as shown in FIG. 3C or FIG. 6C. Alternatively to a combined sensor, dedicated sensors may be used.

The sensors 7m, 7r and/or 7s may comprise any combination of sensors or sensing elements capable of measuring an indication of light intensity, preferably in a time resolved manner. The sensor 7m, 7r and/or 7s may comprise any suitable photo sensor or detector for detecting impinging electromagnetic radiation. Examples may include photodiodes, photomultiplier tubes, phototransistors, photo resistors or light dependent resistors (LDR), photovoltaic cells, active pixel sensors (e.g. CMOS), charge-coupled devices (CCD), or combinations thereof.

Figure 3A:
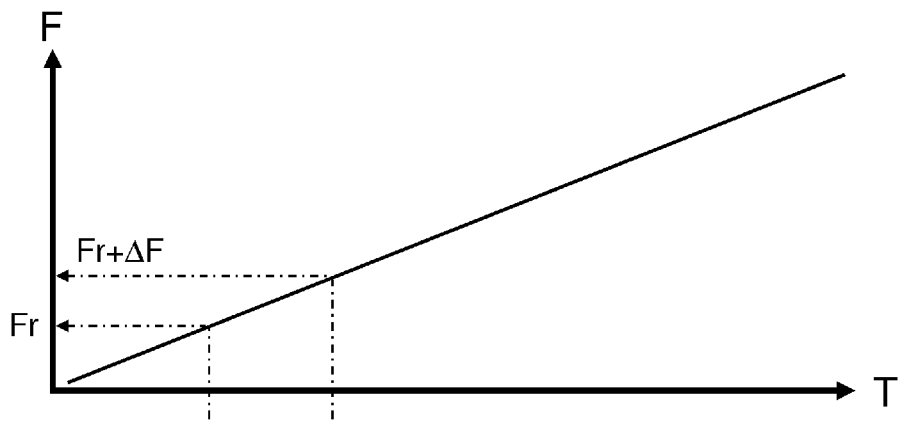
FIG. 3A shows a graph of an optical output frequency of a frequency tunable laser system varying as a function of time.

FIG. 3A shows an example graph of an optical output frequency F of a frequency tunable laser system varying as a function of time T. In the shown graph the frequency F is continuously increased over time T wherein the frequency passes a reference frequency Fr. Of course the frequency F may be varied in any other way, e.g. as shown in FIG. 6A.

Figure 3B:
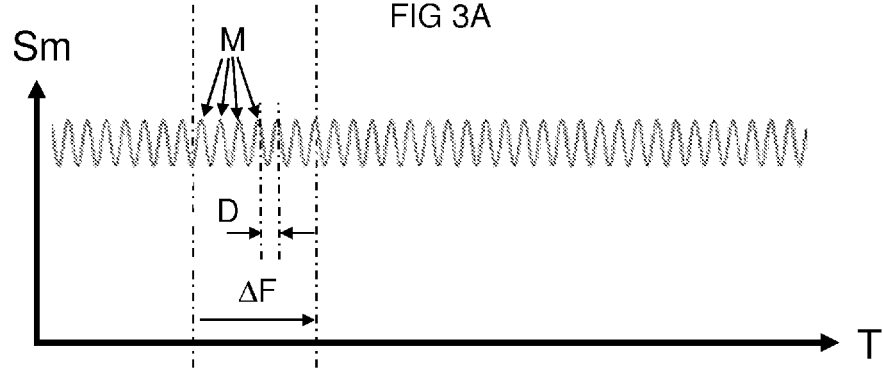
FIG. 3B shows a graph of an intensity modulation of the frequency tunable laser system of FIG. 3A as a function of time.
Figure 3C:
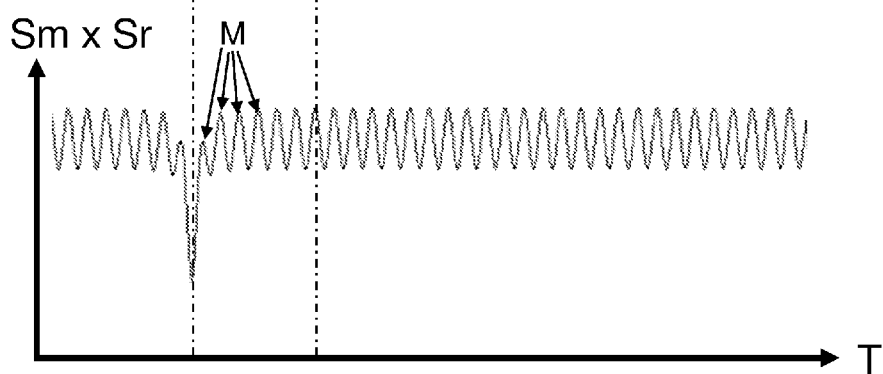
FIG. 3C shows a graph similar to FIG. 3B, further comprising an absorption dip at a reference frequency.

FIG. 3B shows a graph of an intensity modulation signal Sm as a function of time T. The signal Sm may correspond to the signal sent between intensity sensor 7m and the processor 8 shown in FIG. 1 when the optical output frequency F of the laser 2 is varied according to FIG. 3A. The signal Sm comprises a series of oscillations M having an oscillation period D. Each oscillation period D may correspond to a shift in frequency δF of the optical output frequency F of the laser. Without being bound by theory, the frequency shift per oscillation period D may be inversely proportional to the predefined distance between the second reflective surface 2b from which the laser beam is emitted and the external reflective surface 9 (see e.g. FIG. 1). E.g. a functional relation may be:

$$\delta F \sim 1/L, \tag{E1}$$

wherein "δF" is the frequency shift per oscillation and "L" is the predefined distance.

In an embodiment, this may be further specified as:

$$\delta F = Vp \cdot 1/(2L), \tag{E2}$$

wherein "Vp" is the phase velocity of the light along the path between the laser and the external reflecting surface. The phase velocity may be dependent on the refractive index of the medium through which the light travels. In some cases the refractive index may itself be dependent on the optical frequency. In any case, the frequency shift per oscillation may be calculated, if necessary with knowledge of the medium through which the light travels. Alternatively or in addition, the frequency shift per oscillation may be determined through calibration e.g. by shifting the frequency over a known range (e.g. as measured by an external spectrometer) and dividing the total frequency shift by the number of oscillations.

In an embodiment, a processor 8 such as shown in FIG. 1 may calculate the total change in frequency "ΔF" by counting the number of oscillations "Nm" in the signal Sm, e.g. using:

$$\Delta F = Nm \cdot \delta F, \tag{E3}$$

Alternatively or in addition, the processor may calculate ΔF by tracking the total phase Φ (in radians) of the oscillations, e.g. using:

$$\Delta F = \Phi/2\pi \cdot \delta F. \tag{E4}$$

In this way a resolution higher than δF may be achieved. Of course also combinations are possible, e.g. counting the number of oscillations and using the phase to interpolate between oscillations. Also other types of interpolation are possible. While the oscillations are shown as having a sinusoidal behavior, also other shaped oscillations are possible, e.g. the shape of the oscillations may depend on the relative or absolute amount of feedback provided by the reflected part of the laser beam into the cavity such as explained in further detail in the above mentioned article by Giuliani et al. In general, the term "oscillation" as used herein may refer to a period of a periodic or semi-periodic function. The behavior of said periodic or semi-periodic function may change for different frequencies and/or intensities.

The frequency shift per oscillation δF may correlate with a frequency resolution of the laser system, e.g. when not interpolating between oscillations. It is to be appreciated that the frequency resolution may be set by controlling the predefined distance L between the second reflective surface 2b from which the laser beam is emitted and the external reflective surface 9 (see FIG. 1). For example, by increasing L, a frequency resolution may be improved. On the other hand, the number of oscillations per second to be registered may also increase. This may put increased demands on the hardware, e.g. a sampling rate of the sensor and/or a processing rate of the processor. In an embodiment, the predefined distance L is more than 1 centimeter to achieve a preferred minimal frequency resolution. Alternatively or in addition, in an embodiment, the predefined distance L is less than 10 meter to achieve a preferred maximal frequency resolution.

Figure 4A:
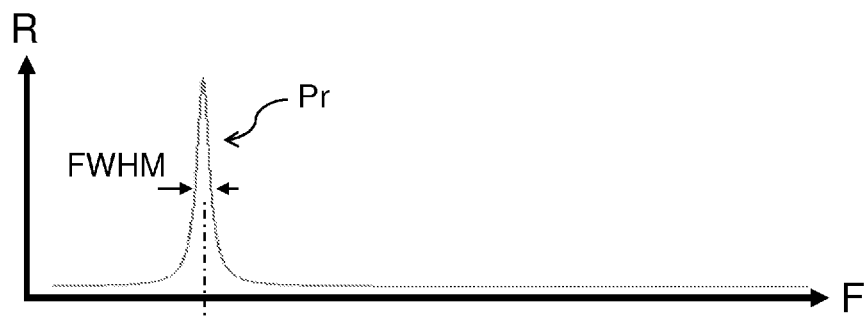
FIG. 4A shows a graph of reflection as a function of frequency for a referencing means.

FIG. 3C shows a graph similar to FIG. 3B, further comprising an dip at a reference frequency Fr. The signal Sm×Sr may correspond to the signal sent between intensity sensor 7m,7r and the processor 8 shown in FIG. 2 when the optical output frequency F of the laser 2 is varied according to FIG. 3A. The signal Sm×Sr may be regarded as a product of the signal Sm of FIG. 3B and a signal Sr having a dip at reference frequency Fr caused by the selective reflectivity curve of the reference filter 10, e.g. an FBG having a uniform transmission except for a reflection peak at frequency Fr, e.g. as shown in FIG. 4A. The processor may optionally use a deconvolution algorithm to separate signal Sm×Sr into signals Sm and Sr for further processing.

In a similar way as described with reference to FIG. 3B, the oscillations M may be used to calculate the change in frequency ΔF of the laser system 1 shown in FIG. 2. Furthermore, using the reference frequency Fr, the processor 8 may calculate an absolute optical frequency F, e.g. using:

$$F=Fr+\Delta F. \quad (E5)$$

Whereas the current figure shows a single reference frequency Fr, also a plurality of reference frequencies may be used. The plurality of reference frequencies may each be used as a reference point from which to start tracking the change in frequency ΔF. Additionally, the said plurality of reference frequencies may be used to calculate the frequency shift per oscillation δF thereby calibrating the system.

In an embodiment (not shown) the referencing means is arranged for providing the processor with two reference frequencies Fr1 and Fr2 during the varying of the optical frequency output of the laser; and the processor is arranged to control the frequency varying means to vary the optical frequency output of the laser between the two reference frequencies Fr1 and Fr2; register the number of oscillations Nr between the reference frequencies Fr1 and Fr2; and calculate the frequency shift per oscillation δF by dividing a frequency difference between the two reference frequencies Fr1 and Fr2 by the number of oscillations Nr between the reference frequencies Fr1 and Fr2. The processor may calculate the frequency shift per oscillation δF, e.g. using:

$$\delta F=(Fr2-Fr1)/Nr \quad (E6)$$

FIG. 4A shows a graph of reflection R as a function of frequency F for a referencing means, e.g. comprising an FBG. The graph may represent a reference spectral signature Pr of the said referencing means. The reference spectral signature Pr of the referencing means comprises a frequency peak at reference frequency Fr, the frequency peak having a full width half maximum FWHM that is smaller than a period D between the oscillations M as a function of the optical frequency F (see FIG. 4B). This may have an advantage that a resolution of the laser system is not limited by the width of the peak of the referencing means.

Figure 4B:
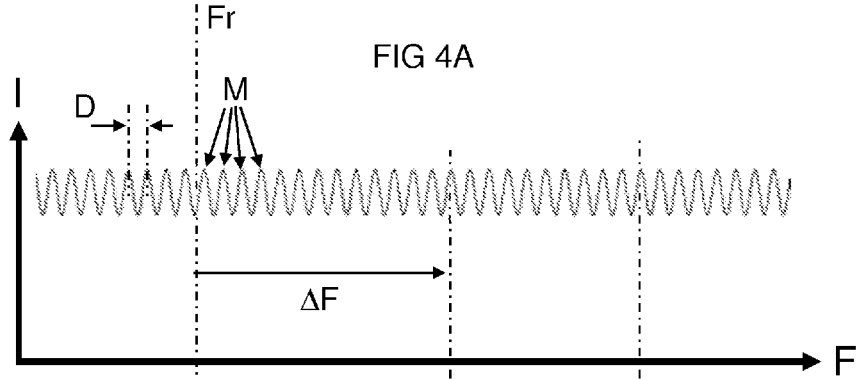
FIG. 4B shows a graph of an intensity output as a function of frequency for a laser influenced by self-mixing interferometry.

FIG. 4B shows a graph of an intensity output I as a function of frequency for a laser influenced by self-mixing interferometry, e.g. the laser system of FIG. 1. When registered by an intensity sensor 7m, e.g. as shown in FIG. 1, this intensity output I may result in a signal Sm. If the frequency F is varied over time T, e.g. as shown in FIG. 3A, the resulting signal Sm may be similar to that of FIG. 3B. If additionally, the referencing means is arranged in a light path of the laser beam between the laser and the sensor 7m,7r as shown in FIG. 2, the resulting signal Sm may be similar to that of FIG. 3C.

In an embodiment the intensity output I is used for calculating the change in optical frequency output ΔF of a frequency tunable laser system, e.g. such as shown in FIG. 1, the method comprising varying the optical frequency output F of the laser; monitoring the intensity output of the laser; registering oscillations M in the intensity output caused by self-mixing interference responsive to the change in optical frequency ΔF; and calculating the change in optical frequency output ΔF from the registered oscillations M of the intensity output I.

Figure 4C:
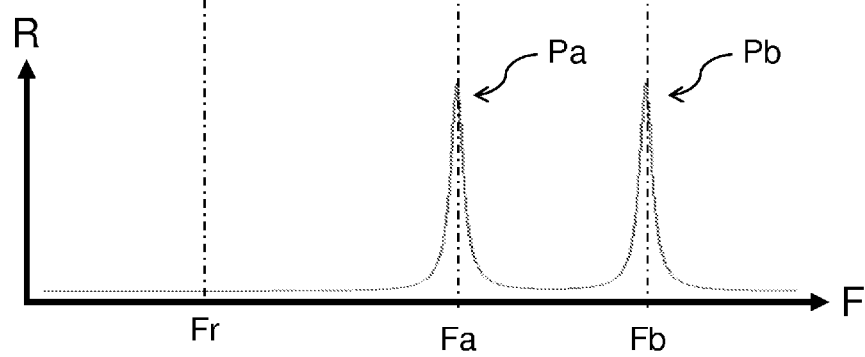
FIG. 4C shows a graph of reflection as a function of frequency for two sensing elements.

FIG. 4C shows a graph of reflection R as a function of frequency F for two optical sensing elements. The graph may represent sensing element spectral signatures Pa and Pb of one or more optical sensing elements. The sensing element spectral signatures Pa and Pb comprise central optical frequencies Fa and Fb, respectively. The optical sensing element may comprise an optical element that can be used for sensing a physical parameter through an influence of said physical parameter on the optical properties of the optical sensing element. The optical sensing elements may comprise e.g. one or more fiber Bragg gratings (FBG), Fabry-Perot cavities, ring resonators, or combinations thereof. The physical parameter may comprise any quantifiable environmental property having a measurable influence on the sensing element spectral signature. The physical parameter may e.g. comprise a temperature of the sensing element, a strain exerted on the sensing element, a refractive index change of the sensing element or a refractive index change of the surrounding medium, or combinations thereof.

The sensing element spectral signature may thus be dependent on one or more physical parameters influencing the sensing element. E.g. the central frequency Fa may shift as a function of the one or more physical parameters. The sensing element spectral signature may comprise one or more frequency dependent optical properties of the optical sensing element. The sensing element spectral signature may be represented by and/or derivable from e.g. a reflection, transmission, and/or absorption spectrum of the sensing element. Also other optical properties of the optical sensing element may be comprised in the sensing element spectral signature such as a frequency dependent polarization rotation in a birefringent material of an optical sensing element.

Figure 5:
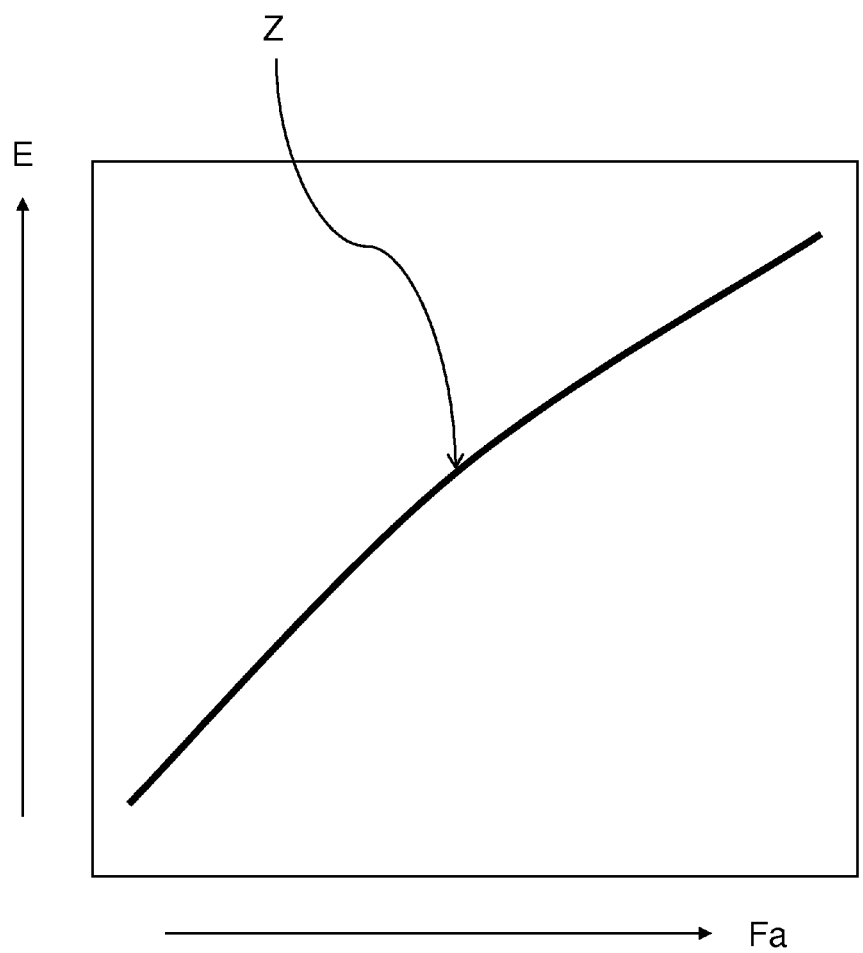
FIG. 5 shows a graph representing a lookup table correlating a sensing element spectral signature to a physical parameter.

FIG. 5 shows a graph Z correlating a central frequency Fa of a sensing element spectral signature e.g. such as shown in FIG. 4C, to a physical parameter E. The graph Z may represent a lookup table. The lookup table may comprise a functional relation between a physical parameter E and an aspect of the sensing element spectral signature. The aspect may be any frequency dependent parameter derivable from the sensing element spectral signature, such as the central frequency of a peak, the weighted average over a range of the spectrum, etcetera. The functional relation may e.g. comprise an analytical function and/or numerical value in a table. The lookup table may also comprise multi-dimensional data, e.g. when the frequency dependent parameter derivable from the sensing element spectral signature is correlated to a plurality of physical parameters. E.g. the central frequency Fa may be a function of both temperature and strain. In an embodiment, the system may comprise a plurality of sensing elements having different functional relations with respect to the plurality of physical parameters. These different functional relations may be measured and decomposed into the individual physical parameters. Alternatively or in addition, a plurality of aspects from a single sensing element may be used.

FIG. 6A shows a graph of an optical output frequency F and intensity I of a frequency tunable laser system varying as a function of time T. As shown the frequency is steadily increased over a first time interval and steadily decreased in a second interval. In this way the frequency may be scanned back and forth over a certain frequency range as a function of time. In the shown scan interval, the frequency F may twice pass a reference frequency Fr. In an embodiment, the varying of the optical output frequency F may be accompanied by a varying of an envelope of the intensity output I of the laser. The envelope of the intensity output may refer to the average intensity output, e.g. averaged over an oscillation period or to the intensity output of the same laser without self-mixing.

Such variation of the envelope may occur e.g. due to variations in the gain of the gain medium of the laser as a function of output frequency. Alternatively or in addition the variation of the envelope may be the result of the way in which the laser frequency is varied, e.g. when variation of the frequency is accompanied by variation in driving current.

In an embodiment the laser 2 comprises a diode laser and the frequency varying means 6 comprises a current source arranged for modulating an electric current through the diode laser wherein the optical frequency output F of the laser 2 is varied by said modulating of the electric current. The amount of current may influence an optical frequency output F of the laser. At the same time the amount of current may influence an intensity output I of the laser. For instance, a refractive index of a gain medium in the cavity may be changed as a function of an electric field applied to the gain medium, which electric field may be a function of the current that is applied to the laser. The change in the refractive index of the gain medium may influence an optical path length in the cavity. This may influence the output frequency of the laser. At the same time the increased current may lead to an increased pumping of the gain medium leading to increased gain of light passing through the gain medium.

Alternatively or in addition the optical output frequency of the laser may be controlled by other means, e.g. by varying a temperature of the laser, e.g. the gain medium. In an embodiment, the frequency varying means comprises refractive index varying means for varying a refractive index of a medium in the cavity for varying the optical frequency output of the laser. Said refractive index varying means may e.g. comprise means for applying a varying electric field to the medium, means for varying a temperature and/or pressure of the medium, or any other means for varying the refractive index of a medium in the cavity.

Figure 6B:
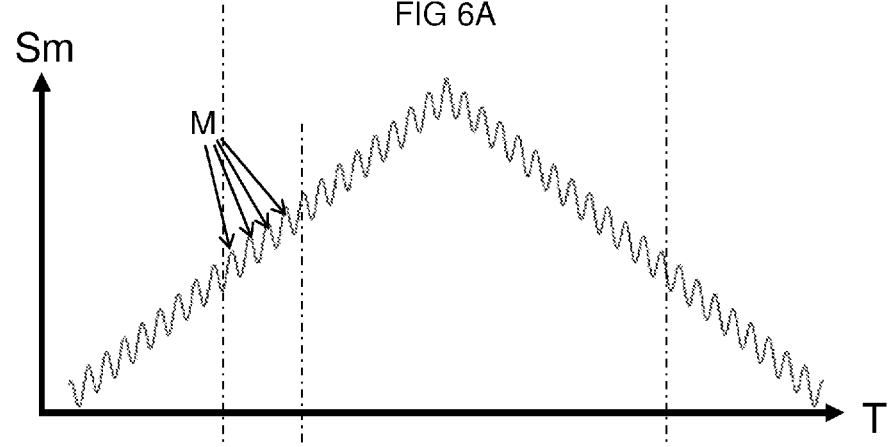
FIG. 6B shows the graph of an intensity modulation of the frequency tunable laser system of FIG. 6A as a function of time with self mixing.
Figure 6C:
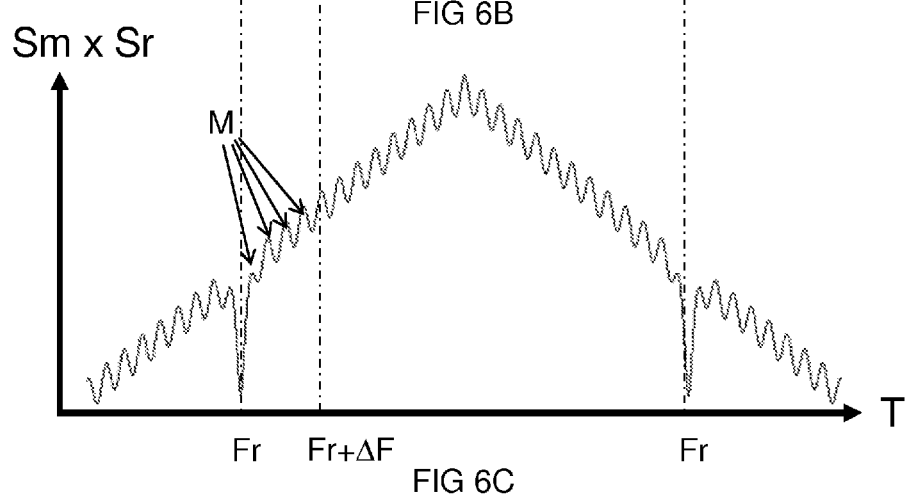
FIG. 6C shows a graph similar to FIG. 6B, further comprising intensity dips at a reference frequency.

FIG. 6B shows a signal Sm indicative of an intensity output of a laser varying its frequency according to FIG. 6A. The signal Sm may correspond to the signal sent between intensity sensor 7m and the processor 8 shown in FIG. 1 when the optical output frequency F of the laser 2 is varied according to FIG. 6A. Similar as in FIG. 3B, the signal comprises a plurality of oscillations M resulting from self-mixing in the laser cavity. On top of this, the intensity output of the laser comprises a continuous rise or fall as a function of frequency which may be attributed to the above mentioned correlation between the frequency and envelope intensity output of the laser, e.g. dependent on the type of laser used and/or the driving mechanism employed by the frequency varying means. In the current example, the envelope intensity output of the laser varies proportional to the frequency output. Alternatively, also other functional relations between the frequency and intensity envelope may exist, e.g. inversely proportional, non-linear, etcetera.

FIG. 6C shows a graph similar to FIG. 6B, further comprising intensity dips at reference frequency Fr. As was noted in FIG. 6A, the frequency F is swept across the reference frequency Fr twice. The signal Sm×Sr may correspond to the signal sent between intensity sensor 7m,7r and the processor 8 shown in FIG. 2 when the optical output frequency F of the laser 2 is varied according to FIG. 6A. The signal Sm×Sr may be regarded as a product of the signal Sm of FIG. 6B and a signal Sr having a dip at reference frequency. In a similar way as described with reference to FIG. 3B, the oscillations M may be used to calculate the change in frequency $\Delta F$ of the laser system 1 shown in FIG. 2. Furthermore, using the reference frequency Fr, the processor 8 may calculate an absolute optical frequency F.

Figure 7:
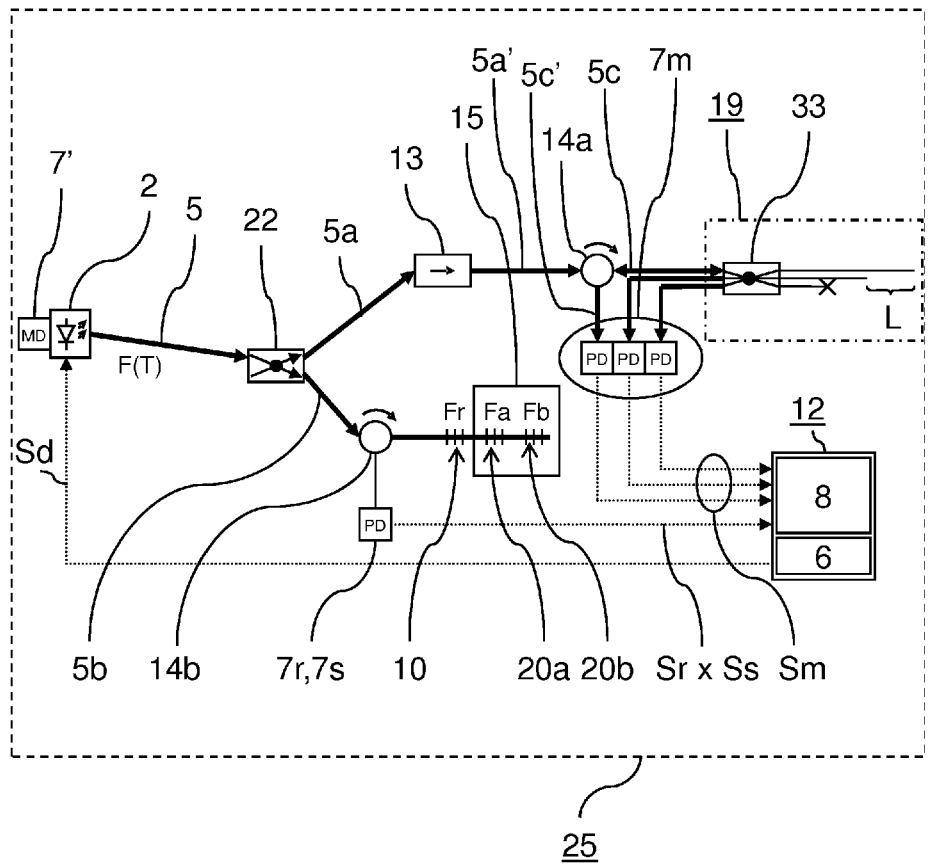
FIG. 7 shows an optical measuring system comprising a frequency tunable laser system having a separate interferometer.
Figure 8:
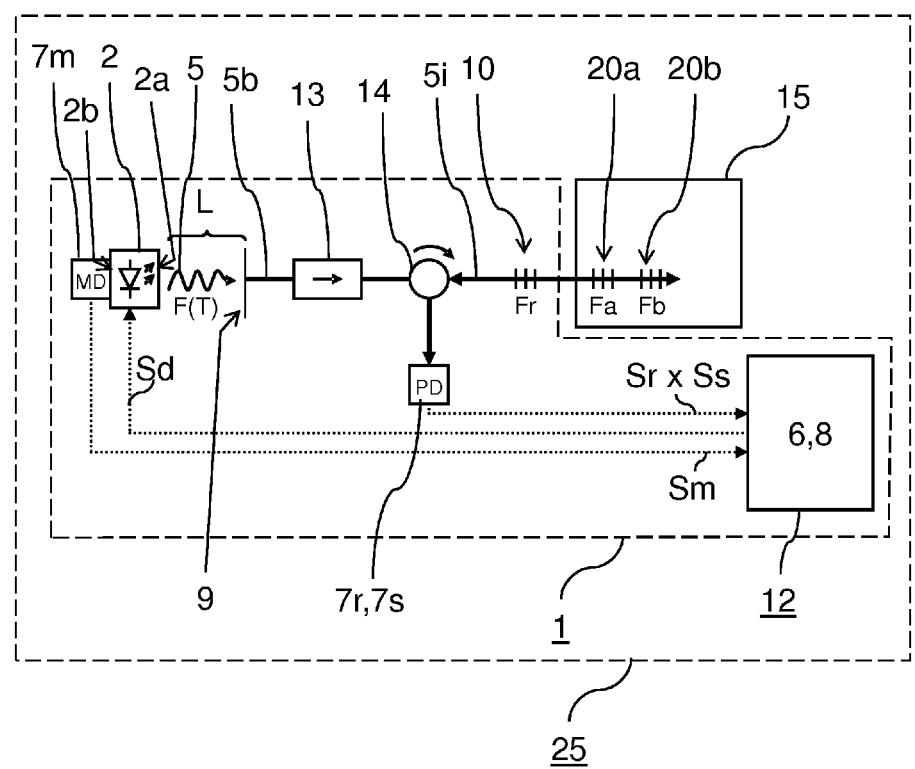
FIG. 8 shows a first embodiment of an optical measuring system comprising a frequency tunable laser system using self-mixing interferometry.

FIG. 7 shows an optical measuring system 25 comprising a frequency tunable laser system having a separate interferometer 19 for tracking a change in optical frequency output of the laser 2. FIG. 7 illustrates a system not using self-mixing interferometry and may be compared e.g. to FIG. 8 wherein self-mixing is used.

In use, electronics 12, comprising processor 8 and frequency varying means 6, drives the laser 2 using driving signal Sd. The driving signal Sd causes laser 2 to vary a frequency output F of emitted laser beam 5 as a function of time T. Laser beam 5 is split by coupler 22 into beams 5a and 5b. Coupler 22 may comprise e.g. a 2×2 fused fiber optic coupler. Alternatively, the coupler 22 may comprise other means such as a beam splitter e.g. a semi-transparent mirror to split the incoming beam 5 into first and second laser beams 5a and 5b.

First laser beam 5a is sent to optical isolator 13 arranged for preventing light from reflecting back through the optical isolator. Beam 5a' passing through optical isolator 13 is sent to optical circulator 14a. Optical circulator 14a is arranged for sending light from incoming pathway 5a' to pathway Sc and incoming light from pathway 5c to pathway Sc'. Alternative to the optical circulator a series of beam splitters may be used to couple the light as described.

Laser beam 5c, coupled out of optical circulator 14a, is sent to interferometer 19. Interferometer 19 comprises coupler 33 to split the light into different paths having a path length difference L. Coupler 33 may comprise a 3×3 fused fiber optic coupler. Upon recombination, the reflected light may interfere constructively or destructively dependent on a relative phase of the light built up in the different path ways. The relative phase may depend on the frequency of the light and the length of the path way difference. Alternative to the shown interferometer 19, any other type of interferometer may be used.

Light reflected back from interferometer 19 is sent to intensity sensors 7m recording the intensity of the light and sending intensity signal Sm proportional to the recorded intensity to processor 8 comprised in electronics 12. Processor 8 may process signal Sm e.g. by counting oscillations caused by the interference of light in the interferometer as a function of a frequency variation of the light. In this way a change in frequency $\Delta F$ of the output light of the laser 2 may be tracked by the processor 8, similarly as explained with reference to FIGS. 3A-3C.

Second beam 5b coupled out of coupler 22, is sent to optical circulator 14b which redirects beam 5b into reference filter 10, e.g. a first FBG reflecting at a reference frequency Fr. Light transmitted through the reference filter 10 reaches first and second sensing elements 20a and 20b which comprises FBGs embedded in a medium 15. The medium may influence sensing element frequencies Fa and Fb at which the sensing elements 20a and 20b reflect light.

Light reflected from the reference filter 10 and sensing elements 20a and 20b is sent back into optical circulator 14b which redirects this light towards sensor 7r, 7s. In the present embodiment, sensor 7r, 7s records both the reference frequency Fr and the sensing element frequencies Fa and Fb. Alternatively, separate sensors may be used to record the frequencies Fr, Fa, and/or Fb, e.g. by using further beam splitters and sensors, wherein the further beam splitters split light into a plurality of beams separately probing different element and wherein the further sensors are used to separately record the spectral signatures of the different elements.

In the present embodiment, combined sensor 7r, 7s sends a signal Sr×Ss being a multiplied signal comprising signals Sr and Ss. The signal Sr×Ss may comprise a series of reflection peaks at frequencies Fr, Fa, and Fb. The reflection peaks may be recorded by processor 8. The processor may identify when laser 2 reaches frequency Fr. Reference frequency Fr may be distinguished e.g. from sensing element frequencies Fa and Fb by setting reference frequency Fr well below or above sensing element frequencies Fa and Fb.

Combining reference frequency Fr derived from signal Sr×Ss and the change in frequency $\Delta F$ derived from signal Sm, an absolute frequency F of the laser 2 may be calculated similarly as explained with reference to FIGS. 3A-3C. The calculated frequency F of the laser 2 may be used to reconstruct spectral signatures of sensing elements 20a and 20b. In particular, the processor may determine the value of sensing element frequencies Fa and Fb and optionally convert these values into a physical parameter of medium 15.

It is noted that laser 2 may optionally comprise a monitoring diode 7' to monitor an intensity output of the laser. The monitoring diode 7' may receive leakage light through a cavity mirror opposite to the out-coupling mirror of the main laser beam. In the present embodiment, the monitoring diode 7' measures a substantially straight i.e. non-oscillating output intensity signal of the laser since the self-mixing interference in the laser cavity by back-reflection of a part of the emitted laser beam is avoided.

FIG. 7 depicts an example of an interrogator system for multiple FBG sensors. In an embodiment, a tunable laser source, e.g. a current-modulated VCSEL, may be used to generate narrow-band optical power at time-varying wavelength. This optical power is, via a 2×2 coupler applied to an interferometer. The external interferometer, in this case comprising a 3×3 coupler and a fixed optical path difference L provides information on the change in wavelength during the scan. The second output of the 2×2 coupler is, via a circulator, connected to a fiber containing a reference fiber Bragg grating (FBG) and several sensor FBG's. The optical power reflected at the reference FBG, with a-priory known wavelength, is measured with a photo diode (PD). A maximum in reflected optical power provides a time-reference of the wavelength emitted by the source. By, combining this information with the phase information obtained with the interferometer, i.e. the wavelength change over time, the emitted wavelength occurring at any moment during the scan can be accurately determined. By finally comparing the measured instantaneous emitted wavelength with maxima in optical power reflected from the sensor FBGs, the wavelength reflected by the sensor FBGs is determined.

As can be seen the system comprises a large number of optical components: 2×2 coupler, 3×3 coupler, two circulators, 4 photo diodes, and many connecting fibers. Moreover, the four PDs may require dedicated analog front-end electronics for read-out. It is to be appreciated that the current disclosure may aid in greatly reducing the complexity of the optical an electronic system, maintaining comparable analytical performance.

FIG. 8 shows a first embodiment of an optical measuring system 25 comprising a frequency tunable laser system 1. The optical measuring system 25 is similar to that shown in FIG. 7 except that the change in frequency is tracked by means of self-mixing interference rather than by means of an external interferometer. It is to be appreciated that by using self-mixing interference, the design of the frequency tunable laser system 1 and optical measuring system 25 may be significantly simplified compared e.g. to the system of FIG. 7.

The shown frequency tunable laser system 1 comprises a laser 2 that in use emits a laser beam 5. The laser beam 5 has an optical frequency output F that is varied as a function of time T by means of a frequency varying means 6 comprised in electronics 12. The system 1 further comprises an intensity sensor 7m arranged for receiving light from the laser 2 and providing an intensity signal Sm that is indicative of an intensity output I of the light from the laser 2. The electronics 12 further comprise a processor 8 arranged for controlling the frequency varying means 6 for varying the optical frequency output F of the laser 2. In use, processor 8 receives the intensity signal Sm from the intensity sensor 7m for monitoring the intensity output of the laser 2.

The frequency tunable laser system 1 further comprises an external reflective surface 9, in use, fixedly arranged in a light path of the laser beam 5 outside the laser cavity at a predefined distance L from the exit point of the laser beam from the cavity of the laser along the light path of the laser beam to reflect part of the emitted laser beam 5 back into the laser cavity.

The processor 8 is further arranged for processing the intensity signal Sm and registering oscillations M of the intensity output caused by interference of the reflected part of the laser beam 5 in the cavity and responsive to the change in optical frequency ΔF. The processor 8 may calculate the change in optical frequency output ΔF from the registered oscillations M of the intensity output and predefined distance L, e.g. as explained with reference to FIG. 3B.

In an embodiment, laser system 1 comprises an optical isolator 13 arranged in the light path of the laser beam 5 for preventing back-reflections from components other than the external reflective surface 9 into the cavity. The optical isolator may provide a better control over the amount of back-reflected light.

In an embodiment, the intensity sensor 7m comprises a monitoring diode MD arranged for receiving light through the first reflective surface 2a and sending the intensity signal Sm comprising the modulations M used for calculating the change in optical frequency output ΔF to the processor 8. Preferably, a laser 2 is used with a built in monitoring diode. E.g. VCSEL lasers may be provided with a monitoring diode. The light for monitoring the intensity oscillations resulting from self-mixing may also be provided e.g. though light scattering out of the cavity. In any case the monitoring diode does not have to be placed in the main output beam 5 emitted from the second cavity mirror 2b. No extra beam splitter is thus required. This may contribute further to a laser system of simpler design, e.g. a more compact laser system.

In use, the output frequency of the laser 2 is varied by electronics 12 through driving signal Sd. Laser beam 5b passing through the external reflective surface 9 is sent through optical isolator 13 and into optical circulator 14. From here light is directed as beam 5i into reference filter 10 and sensing elements 20a and 20b embedded in medium 15. Light reflected back from elements 10, 20a, and 20b is redirected by optical circulator 14 to impinge onto sensor 7r, 7s. Sensor 7r, 7s sends signal Sr×Ss to processor 8 comprised in electronics 12. The signal Sr×Ss may comprise a series of reflection peaks at frequencies Fr, Fa, and Fb. The reflection peaks may be recorded by processor 8. The processor may identify when laser 2 reaches frequency Fr. Reference frequency Fr may be distinguished e.g. from sensing element frequencies Fa and Fb by setting reference frequency Fr well below or above sensing element frequencies Fa and Fb.

In an embodiment referencing means are provided comprising a reference filter 10 arranged in a light path of the laser 2, the reference filter 10 having a reference filter frequency spectrum comprising a reference spectral signature at a reference frequency Fr. The referencing means further comprise a reference sensor 7r arranged for registering the reference filter frequency spectrum during the varying of the optical frequency output F of the laser 2, and providing the processor 8 with the reference frequency Fr when the reference spectral signature Pr is detected. Alternatively or in addition other referencing means may be provided.

In an embodiment, the referencing means are arranged for providing the processor 8 with a reference frequency Fr during the varying of the optical frequency output F of the laser 2. The processor 8 is further arranged for calculating the optical frequency output F of the laser by tracking the change in optical frequency output ΔF relative to the reference frequency Fr.

A reduction in complexity may thus be achieved e.g. compared to the employment of the external interferometer 19 of FIG. 7 by self-mixing interferometry, such that the system reduces to the system depicted in FIG. 8. In the present disclosure the external cavity ("L" in FIG. 8) may be known or determinable and the changes in optical output during current modulation may be analyzed to determine changes in wavelength emitted by the laser as function of time. Absolute wavelength information may be obtained by combining the information from self mixing interferometry using referencing means, e.g. the reflection at a reference FBG. This wavelength information as function of time can e.g. be correlated to the maxima in reflected power as function of time from the sensor FBGs in order to determine the wavelength response of the sensor FBGs. The optical power emitted by the laser can advantageously be measured using a monitoring diode (MD) which may be already present in most packaged VCSELs, hence no extra components may be required. In an embodiment, the external cavity may be obtained by a well-controlled fixed spacing between the laser diode and a fiber transporting the optical power to the FBGs. Part of the power emitted by the laser may reflect from the end of the fiber back into the laser cavity.

The amount of power back-reflected into the laser cavity by the external mirror 9 is preferably less than 5% of the emitted laser power. In this power feedback regime, the laser may still function without too much interference, e.g. may exhibit predictable periodic behavior. Furthermore, the transmitted power may still be sufficiently high for satisfactory detection of the sensor elements, e.g. the FBGs.

The amount of power back-reflected into the laser cavity by the external mirror 9 is preferably sufficiently high for accurate detection of the self-mixing interference. The amount of power back-reflected into the laser cavity may be any above-zero amount of power, e.g. such that a signal to noise ratio, i.e. a ratio of a variation of the laser power as a function of self-mixing over other noise variations in the laser output power, is higher than a certain minimum detection value. The minimum value for the power back-reflected into the laser cavity may also be related to the total emitted power, e.g. preferably more than 1E-7 percent of the emitted laser power.

Figure 9:
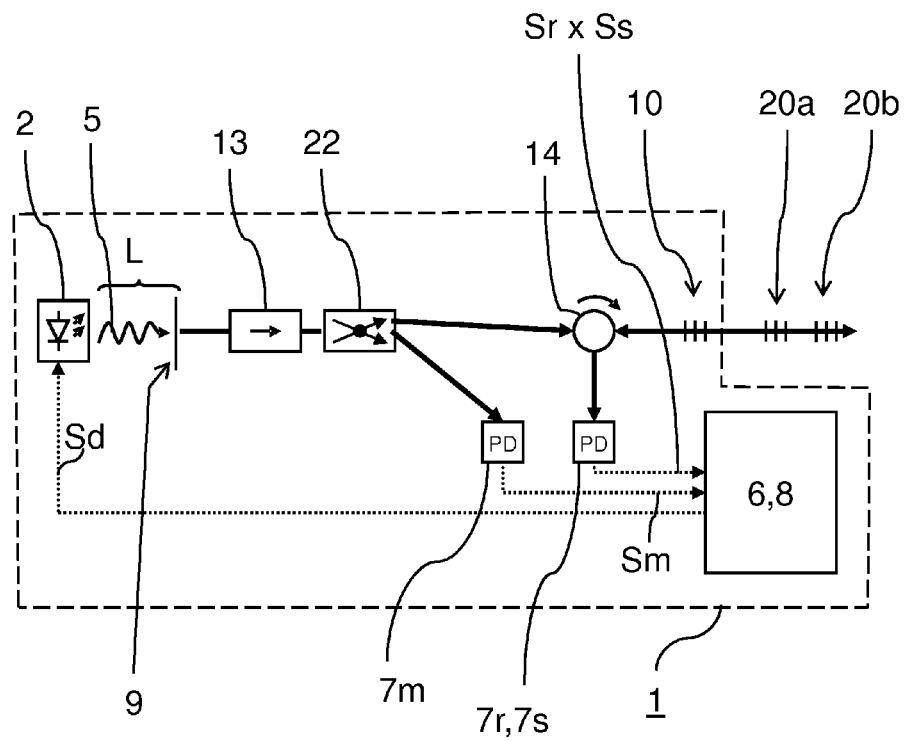
FIG. 9 shows a second embodiment of an optical measuring system comprising a frequency tunable laser system using self-mixing interferometry.

FIG. 9 shows a second embodiment of an optical measuring system comprising a frequency tunable laser system using self-mixing interferometry. This embodiment is similar to the one shown in FIG. 8 except that instead of an internal monitoring diode, a dedicated external monitoring diode 7m is used. In the shown embodiment, coupler 22 is used to send a fraction of the optical power to dedicated sensor 7m used to monitor the optical power emitted by the laser 2. The coupler 22 could for instance be a 90:10 coupler, wherein 10% of the light is coupled directly to the sensor 7m. The modulating signal Sm is thus received from external intensity sensor 7m. An advantage of a dedicated photo-diode as opposed to a built-in monitoring diode may be increased flexibility of the system. A further advantage may be that a laser may be used for which a monitoring diode may be impractical. Further details and components of this embodiment are similar as described in FIGS. 7 and 8.

Figure 10:
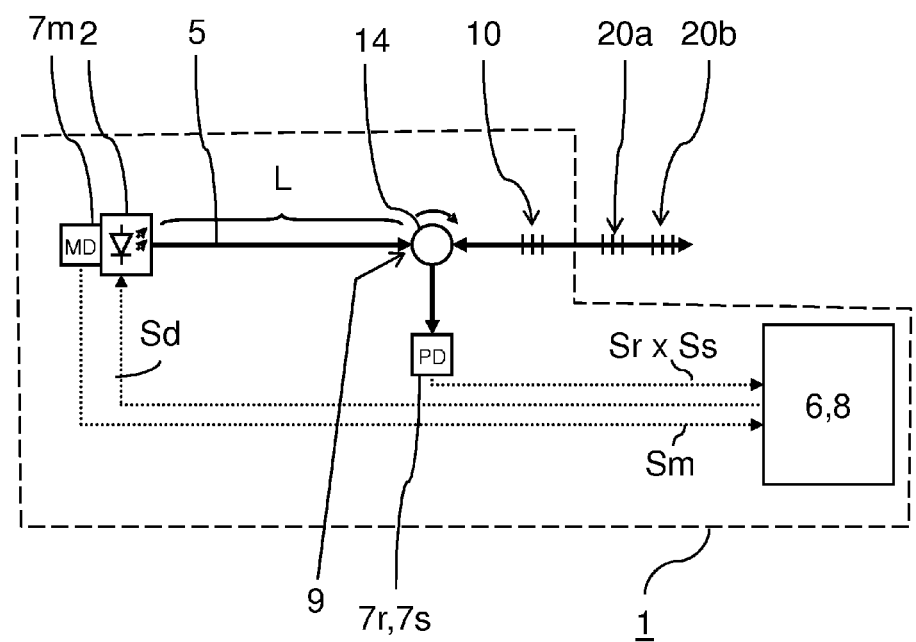
FIG. 10 shows a third embodiment of an optical measuring system comprising a frequency tunable laser system using self-mixing interferometry.

FIG. 10 shows a third embodiment of an optical measuring system 25 comprising a frequency tunable laser system 1 using self-mixing interferometry. This embodiment is similar to the one shown in FIG. 8 except that instead of a dedicated external reflective surface 9, a stray reflection from a non-dedicated optical component is used. In this embodiment optical feedback may result from the non-ideal properties of the circulator, i.e. part of the optical power is reflected back into the laser from the input port of the circulator. The predefined distance L is thus defined by the distance between the laser 2 and the circulator 14.

An advantage of this embodiment may be a further reduction in optical parts. An advantage of a dedicated external reflective surface such as shown in FIG. 8 may be a better control over the distance L, the direction of the back-reflections, and/or the amount of power reflected. Further details and components are similar as described in FIGS. 7 and 8.

Figure 11:
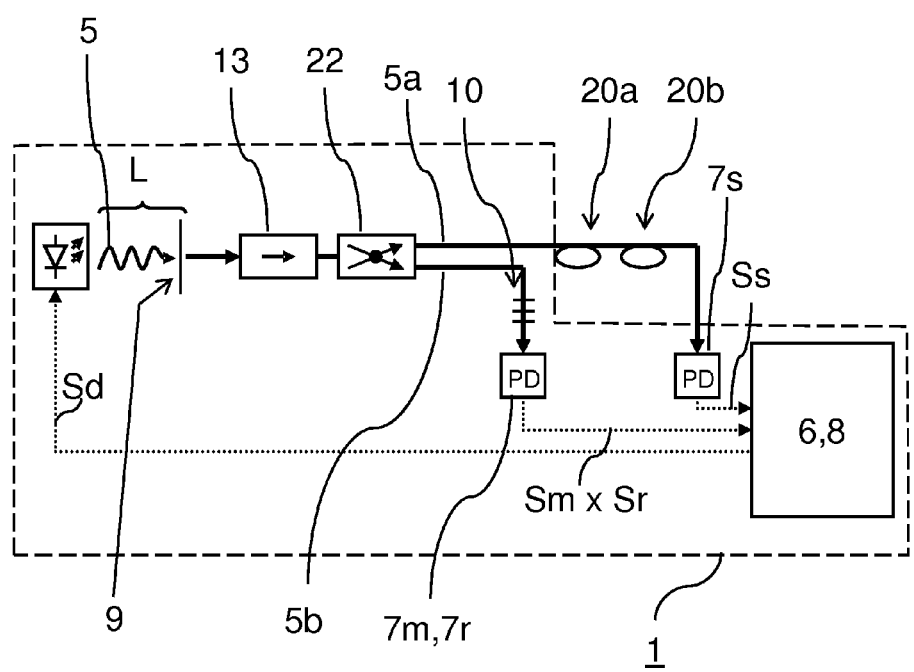
FIG. 11 shows a fourth embodiment of an optical measuring system comprising a frequency tunable laser system using self-mixing interferometry.

FIG. 11 shows a fourth embodiment of an optical measuring system 25 comprising a frequency tunable laser system 1 using self-mixing interferometry. The frequency tunable laser system 1 of this embodiment is similar to that shown in FIG. 2 but further comprising a sensor 7s reading out sensing elements 20a and 20b. In this embodiment the sensing elements are comprised of a plurality of ring resonators (with varying nominal ring length) that are interrogated via the through port (in transmission). The referencing means 10 is located in the second branch 5b to prevent interference with the ring resonator response measurement. It is noted that in this embodiment, the sensor 7s is dedicated to recording output from sensors 20a and 20b while sensor 7m, 7r measures both the self-mixing caused modulations of the laser and the reference wavelength of the referencing means 10. The sensor 7m, 7r may send a signal Sm×Sr to processor 8, the signal comprising a modulating signal Sm and a reference frequency signal Sr, e.g. as shown in FIG. 6C.

Figure 12:
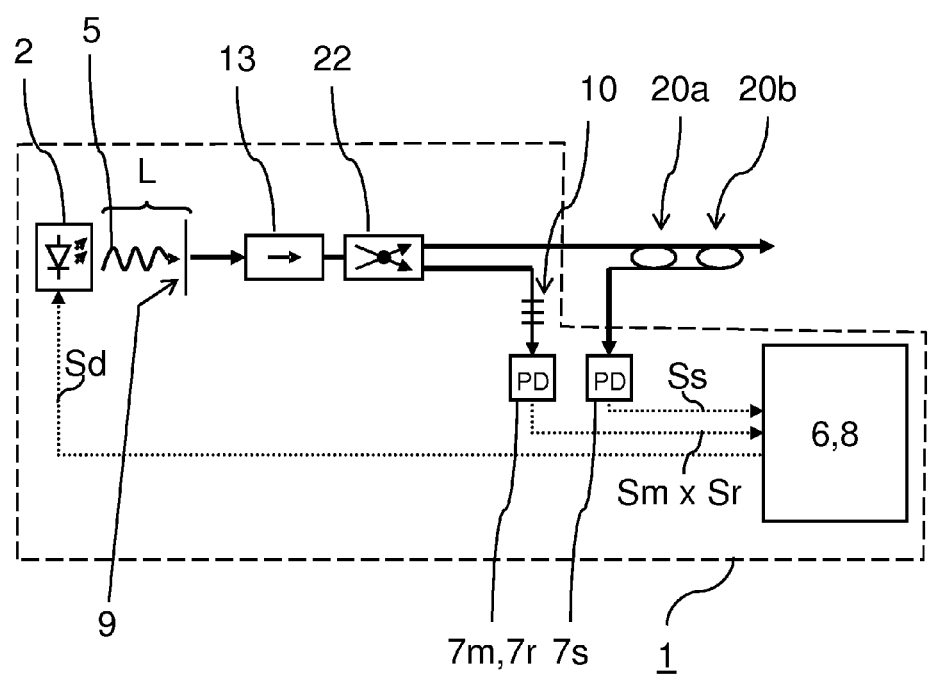
FIG. 12 shows a fifth embodiment of an optical measuring system comprising a frequency tunable laser system using self-mixing interferometry.

FIG. 12 shows a fifth embodiment of an optical measuring system comprising a frequency tunable laser system using self-mixing interferometry. In this embodiment a plurality of ring resonators (with varying nominal ring length) is interrogated via the drop port (in reflection).

While example setups of optical components were shown, also alternative systems and means may be used for achieving similar results. E.g. optical components may be combined or split up into one or more alternative optical components having similar results. Similarly electrical components may be split into separate and/or dedicated components or be comprised in integrated circuitry. The various elements of the embodiments as discussed and shown offer certain advantages, such as providing a frequency tunable laser system of simpler design. Of course, it is to be appreciated that any one of the above embodiments or processes may be combined with one or more other embodiments or processes to provide even further improvements in finding and matching designs and advantages. It is appreciated that this invention offers particular advantages to optical measuring systems, and in general can be applied for any application wherein a frequency tunable laser is used.

Finally, the above-discussion is intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the broader and intended spirit and scope of the present system as set forth in the claims that follow. The specification and drawings are accordingly to be regarded in an illustrative manner and are not intended to limit the scope of the appended claims.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise; no specific sequence of acts or steps is intended to be required unless specifically indicated; and no specific ordering of elements is intended to be required unless specifically indicated.

The invention claimed is:

1. Frequency tunable laser system comprising
a laser with first and second reflective surfaces defining a laser cavity with a laser gain medium between the first and second reflective surfaces, wherein the second reflective surface is semi-transparent for emitting, in use, a laser beam from the second surface;
frequency varying means arranged for varying an optical frequency output of the laser;
an intensity sensor arranged for receiving light from the laser and providing an intensity signal that is indicative of an intensity output of the light from the laser;
a processor arranged for
controlling the frequency varying means for varying the optical frequency output of the laser; and
receiving the intensity signal from the intensity sensor for monitoring the intensity output of the laser; wherein
the frequency tunable laser system further comprises an external reflective surface, in use, fixedly arranged in a light path of the laser beam outside the laser cavity at a predefined distance from the second reflective surface along the light path of the laser beam to reflect part of the emitted laser beam back into the laser cavity; and wherein
the processor is further arranged for
processing the intensity signal and registering oscillations of the intensity output caused by interference of the reflected part of the laser beam in the cavity and responsive to a change in optical frequency as a result of the varying of the optical frequency output of the laser; and
calculating the change in optical frequency output from the registered oscillations of the intensity output and predefined distance.

2. Frequency tunable laser system according to claim 1, further comprising:
referencing means arranged for providing the processor with a reference frequency during the varying of the optical frequency output of the laser, wherein
the processor is further arranged for
calculating the optical frequency output of the laser by tracking the change in optical frequency output relative to the reference frequency.

3. Frequency tunable laser system according to claim 2 wherein the referencing means comprises
a reference filter arranged in a light path of the laser, the reference filter having a reference filter frequency spectrum comprising a reference spectral signature at the reference frequency; and
a reference sensor arranged for registering the reference filter frequency spectrum during the varying of the optical frequency output of the laser, and providing the processor with the reference frequency when the reference spectral signature is detected.

4. Frequency tunable laser system according to claim 3 wherein the reference spectral signature comprises a frequency peak having a full width half maximum that is smaller than a period between the oscillations as a function of the optical frequency.

5. Frequency tunable laser system according to claim 1, further comprising
a clock arranged for providing the processor with an indication of time; wherein
the processor is further arranged for:
recording the optical frequency output and/or the change in optical frequency output as a function of time.

6. Frequency tunable laser system according to claim 1, further comprising
an optical isolator arranged in the light path of the laser beam for preventing back-reflections from components other than the external reflective surface into the cavity.

7. Frequency tunable laser system according to claim 1 wherein the laser comprises a diode laser and the frequency varying means comprises a current source arranged for modulating an electric current through the diode laser wherein the optical frequency output of the laser is varied by said modulating of the electric current.

8. Frequency tunable laser system according to claim 1 wherein the intensity sensor comprises a monitoring diode arranged for receiving light through the first reflective surface and sending the intensity signal comprising the modulations used for calculating the change in optical frequency output to the processor.

9. Optical measuring system comprising
a frequency tunable laser system according to claim 1; and further comprising
a sensor comprising
an optical sensing element arranged for receiving output from the laser system and transmitting and/or reflecting a sensing output comprising a sensing element spectral signature;
a sensing detector arranged for receiving the transmitted and/or reflected sensing output;
wherein the processor is further arranged for
reading out the sensing detector as a function of the varying optical frequency output of the laser; and
recording the sensing element spectral signature.

10. Optical measuring system according to claim 9, wherein the sensing element spectral signature is dependent on a physical parameter of the optical sensing element, the optical measuring system further comprising
a lookup table comprising correlations between the sensing element spectral signature and the physical parameter;
wherein the processor is further arranged for
using the lookup table to calculate the physical parameter.

11. Optical measuring system according to claim 9, wherein the optical sensing element comprises one or more fiber Bragg gratings and/or ring resonators.

12. Method for tuning a frequency tunable laser system comprising
a laser with first and second reflective surfaces defining a laser cavity with a laser gain medium between the first and second reflective surfaces, wherein the second reflective surface is semi-transparent for emitting, in use, a laser beam from the second surface;
frequency varying means arranged for varying an optical frequency output of the laser;
an intensity sensor arranged for receiving light from the laser and providing an intensity signal that is indicative of an intensity output of the light from the laser;

the method comprising
- controlling the frequency varying means for varying the optical frequency output of the laser; and
- receiving the intensity signal from the intensity sensor for monitoring the intensity output of the laser; wherein the frequency tunable laser system further comprises an external reflective surface in use, fixedly arranged in a light path of the laser beam outside the laser cavity at a predefined distance from the second reflective surface along the light path of the laser beam to reflect part of the emitted laser beam back into the laser cavity; and wherein the method further comprises
- processing the intensity signal and registering the oscillations of the intensity output caused by interference of the reflected part of the laser beam in the cavity and responsive to the change in optical frequency; and
- calculating the change in optical frequency output from the registered oscillations of the intensity output and predefined distance.

13. Method according to claim 12, further comprising providing
- referencing means arranged for providing a reference frequency during the varying of the optical frequency output of the laser, and wherein the method further comprises
- calculating the optical frequency output of the laser by tracking the change in optical frequency output relative to the reference frequency.

14. Method for measuring a sensor, comprising
tuning a frequency tunable laser system according to claim 12, the method further comprising providing
a sensor comprising
- an optical sensing element arranged for receiving output from the laser system and transmitting and/or reflecting a sensing output comprising a sensing element spectral signature;
- a sensing detector arranged for receiving the transmitted and/or reflected sensing output;

wherein the method further comprises
- reading out the sensing detector as a function of the varying optical frequency output of the laser; and
- recording the sensing element spectral signature.

15. Method according to claim 14, wherein the sensing element spectral signature of the optical sensing element is dependent on a physical parameter of the optical sensing element, the method further comprising providing
- a lookup table comprising correlations between the sensing element spectral signature and the physical parameter;

wherein the method further comprises
- using the lookup table to calculate the physical parameter.

* * * * *